United States Patent [19]

Fehder

[11] Patent Number: 5,179,002
[45] Date of Patent: Jan. 12, 1993

[54] APPARATUS FOR DETERMINING WHETHER RESPIRATORY GAS IS PRESENT IN A GASEOUS SAMPLE

[75] Inventor: Carl G. Fehder, Collingswood, N.J.

[73] Assignee: Nellcor Incorporated, Hayward, Calif.

[21] Appl. No.: 696,281

[22] Filed: Apr. 25, 1991

Related U.S. Application Data

[63] Continuation of Ser. No. 241,298, Sep. 7, 1988, abandoned, which is a continuation of Ser. No. 136,600, Dec. 22, 1987, abandoned, which is a continuation of Ser. No. 896,360, Aug. 13, 1986, Pat. No. 4,728,499.

[51] Int. Cl.$^5$ .................. C12Q 1/26; G01N 31/22; G01N 33/497
[52] U.S. Cl. .................. 435/25; 128/719; 422/56; 422/57; 422/58; 422/87; 436/133; 436/163; 436/167; 436/169
[58] Field of Search .................. 422/56–58, 422/87; 436/133, 163, 167, 169; 128/719; 435/25

[56] References Cited

U.S. PATENT DOCUMENTS

| | | | |
|---|---|---|---|
| 2,136,236 | 11/1938 | Draper | 436/133 X |
| 3,373,735 | 3/1968 | Gallagher | 422/58 X |
| 3,467,601 | 9/1969 | Brauer | |
| 3,505,022 | 4/1970 | Luckey | 436/133 X |
| 3,694,164 | 9/1972 | Guenther | |
| 3,830,630 | 8/1974 | Kiefer et al. | 436/133 X |
| 4,144,306 | 3/1979 | Figueras | 422/56 |
| 4,548,906 | 10/1985 | Sekikawa et al. | 436/113 |
| 4,691,701 | 9/1987 | Williams | 128/207.14 |
| 4,790,327 | 12/1988 | Despotis | 422/85 X |
| 4,879,999 | 11/1989 | Leiman et al. | 128/207.14 |

FOREIGN PATENT DOCUMENTS

| | | | |
|---|---|---|---|
| 592882 | 2/1960 | Canada | 436/133 |
| 1007525 | 8/1955 | Fed. Rep. of Germany | |
| 1043988 | 9/1966 | United Kingdom | |

OTHER PUBLICATIONS

Berman, et al., "The Einstein Carbon Dioxide Detector", Anesthesiology 60, (1984), pp. 613–614.

*Primary Examiner*—Jill A. Johnston
*Attorney, Agent, or Firm*—William E. Pelton

[57] ABSTRACT

A method and apparatus are is disclosed for determining whether respiratory gas is present in a gaseous sample. The sample is brought into contact with an indicator which yields an indication within a diagnostically effective period of time of the presence in the sample of carbon dioxide in concentration of at least 2% while an indication of the presence of carbon dioxide or other trace acidic gas in a sample of ambient air is delayed beyond a predetermined period of time. The method and apparatus of the present invention have particular utility in determining the correct placement of an endotracheal catheter in a patient or in the direction of apnea.

25 Claims, 1 Drawing Sheet

APPARATUS FOR DETERMINING WHETHER RESPIRATORY GAS IS PRESENT IN A GASEOUS SAMPLE

This is a continuation of application Ser. No. 241,298, filed Sep. 7, 1988, now abandoned, which in turn is a continuation of application Ser. No. 136,600, filed Dec. 22, 1987, now abandoned, which in turn is a continuation of application Ser. No. 896,360, filed Aug. 13, 1986, now U.S. Pat. No. 4,728,499.

FIELD OF THE INVENTION

The present invention relates to medical diagnostic techniques and instrumentation with respect to detecting and treating respiratory failure in a patient and in particular to a method and apparatus for determining whether respiratory gas is present in a gaseous sample collected from a patient. The invention has particular utility in determining the correct placement of an endotracheal catheter in a patient and in the detection of apnea.

BACKGROUND OF THE INVENTION

This application is a continuation of U.S. application Ser. No. 136,600 which is a continuation of U.S. application Ser. No. 896,360, now U.S. Pat. No. 4,728,499.

It is understood that exhaled respiratory gas contains a substantially higher concentration of carbon dioxide, usually on the order of 3% to 5%, than does ambient air which normally contains about 0.03% carbon dioxide. Accordingly, the detection of a sufficient concentration of carbon dioxide in a gaseous sample can be considered evidence of respiratory gas.

Numerous techniques and devices which detect the presence of carbon dioxide in a gaseous sample have been disclosed or suggested heretofore. One such technique involves the detection of carbon dioxide through the use of certain chemical compounds which change color according to the pH of their environment. The utility of such chromogenic pH-sensitive indicators in connection with the detection of carbon dioxide is well understood. For example, U.S. Pat. No. 2,890,177 discloses a highly sensitive liquid chemical indicator capable of detecting the presence of carbon dioxide in the range of about $\frac{1}{2}$% concentration or less. U.S. Pat. No. 3,068,073 discloses a method of detecting the relatively low concentration of carbon dioxide found in air. The principal utility disclosed is for field or plant use and neither of these references addresses the problems of detecting the presence of carbon dioxide when it is present in diagnostically significant concentrations, i.e., on the order of about 2% to about 5%.

U.S. Pat. No. 3,114,610 discloses a continuous sampling gas analyzer comprising a pH-sensitive dye suspended in a gel substance, a gas-permeable membrane, a light source for illuminating the dye and a detector for analyzing the light transmitted through the dye. U.S. Pat. No. 3,754,867 discloses a gas analyzer which also uses a light source and which transmits light through a multi-layered sensor unit. A detector analyzes the color change of a pH-sensitive indicator in one of the layers. The color change is apparently a function of the concentration of carbon dioxide in the gas being measured. In U.S. Pat. No. 2,136,236 to Draper complex and expensive equipment is disclosed for use in monitoring the carbon dioxide content of anaesthetic gas going to a patient by bubbling the gas through bulk liquids.

The various devices and compositions disclosed in the above-mentioned patents provide means for detecting or indicating the presence of carbon dioxide under certain circumstances. However, none of these references directly addresses the problem of determining accurately and rapidly the correct positioning of an endotracheal catheter or the detection of an apneic patient.

Introduction of a catheter in the trachea of a human may be required for a number of reasons. For example, in a hospital, an endotracheal catheter, may be used for general anesthesia; in the field, an endotracheal catheter may be needed to resuscitate an apneic patient. In both of these instances, and others, it is critical that the catheter be properly placed in the trachea and not, for example, in the esophagus. If the catheter is improperly placed and the error is not discovered within a very short time, on the order of less than about 20 seconds and preferably within about 2 to about 10 seconds, the patient may begin to suffer irreparable harm or even death.

In view of the criticality of rapid determination of when an endotracheal catheter is improperly placed, the need for a simple device which will rapidly and reliably give an indication of improper (or proper) placement is evident. One early attempt to simplify, expedite and make safe the technique of introduction of an intratracheal catheter is disclosed in U.S. Pat. No. 2,638,096. There, a perforate whistle is adapted to sound an audible signal in the presence of feeble breathing. Such a device has obvious drawbacks and never achieved substantial popularity in the medical field. A complete review of the problems inherent in esophageal intubation and various available techniques for properly locating the catheter is set forth in an article by P. K. Birmingham et al., "Esophageal Intubation: A Review of Detection Techniques." Anesth. Analg. 1986. 65, pp. 886-891.

Several efforts have been made heretofore to construct apparatus capable of detecting carbon dioxide in exhaled breath and thereby ensure proper location of an endotracheal catheter. One such technique, known as capnography, provides a continuous record of expired carbon dioxide, called a capnogram. Such techniques are disclosed by Z. Kalenda in Resuscitation 6, 259-263 1978. Capnography equipment is complex, expensive and often involves infrared spectroscopy.

Relatively less complicated techniques and devices have been also suggested for use in confirming intratrachel placement of a catheter. For example, Berman et al. in Anesthesiology Vol. 60, No. 6 June 1984 disclosed the use of a bulk liquid solution through which exhaled air is bubbled. The bulk liquid solution is contained within a DeLee mucus trap and consists of a mixture of 3 ml of phenophthalein and 3 ml cresol red. Respiratory carbon dioxide causes a color change in the solution. The device of Berman et al., however, is not easily transportable, functions properly only in one position and poses an inherent risk to the patient insofar as improper use might cause the solution to flow into the patient. U.S. Pat. No. 4,691,701 to Williams also purports to relate to determining the location of the endotracheal tube in a patient and the use of a particular type of carbon dioxide detector. However, Williams fails to disclose the capability of or any basis for distinguishing within a relatively rapid period of time between respiratory gas and, for example, ambient air.

SUMMARY OF THE INVENTION

The foregoing and other disadvantages are eliminated by the present method and apparatus in which a gaseous sample is collected from a patient and is brought into contact with a non-fluid detector capable of indicating a response to the presence of at least 2% concentration of carbon dioxide in the sample within a diagnostically effective period of time. In the preferred embodiment, the detector consists of an inert adsorbant and/or absorbant bibulous substrate carrier which may be fibrous or porous and which has been treated with an indicator composition sensitive to predetermined concentrations of carbon dioxide. The indication of the presence of carbon dioxide in predetermined concentrations is preferably in the form of an observable color change of the detector but may also constitute other forms of analogue or digital indications such as might be provided by an electrically responsive device.

In accordance with a preferred embodiment of the present invention the detector is contained within an enclosure having an inlet and an outlet and which is adapted to permit the detector to be viewed. The inlet is placed in fluid flow communication with, for example, an endotracheal catheter so that a gaseous breath sample may be collected within the enclosure. The detector consists of a suitable inert substrate carrier to which has been applied a suitable chemical treatment composition such as an alkaline indicator solution of pH optimally but not necessarily in the range of from about 9.0 to about 10.2 and which consists of a non-volatile hygroscopic, colorless, transparent water soluble liquid and a chromogenic pH-sensitive dye. The composition is preferably such that no color change occurs for approximately ten (10) to fifteen (15) minutes when the detector is exposed to ambient air which has a concentration of 0.03% carbon dioxide as well as small amounts of sulfur dioxide and hydrogen sulfide, but a color change is produced within less than about 20 seconds and preferably within about two (2) to about ten (10) seconds when the detector is exposed to a gaseous sample containing at least about 2% carbon dioxide. For example, this may occur in a particular solvent system when the pK of the dye relative to the pH of the alkaline composition is sufficiently lower thereby to ensure that in ambient air a noticeable color change does not occur for approximately ten (10) to fifteen (15) minutes.

The substrate carrier may be any inert suitably adsorbent or absorbent material to which the treatment solution has been applied either by impregnation or as a coating. Once it has been applied to the carrier, the treatment solution may be dried, to remove excess indicator composition to open the pore structure to gas interface, and it does not flow or migrate or otherwise separate from the carrier while the device is in use.

Since the responsive color change is essentially an interface phenomenon, the carrier is selected so as to provide an appropriate internal surface area. Ideally, the substrate material is such as to maximize the interfacial area per given amount of substrate. The carrier is preferably bibulous, fibrous and/or porous and may be, for example, filter paper or synthetic fibrous material including beads. Other materials which may be used for the carrier include clay, natural fibers such as cotton, various plastics, inorganic crystals, and the like.

DESCRIPTION OF THE PREFERRED EMBODIMENTS

Figure 1:
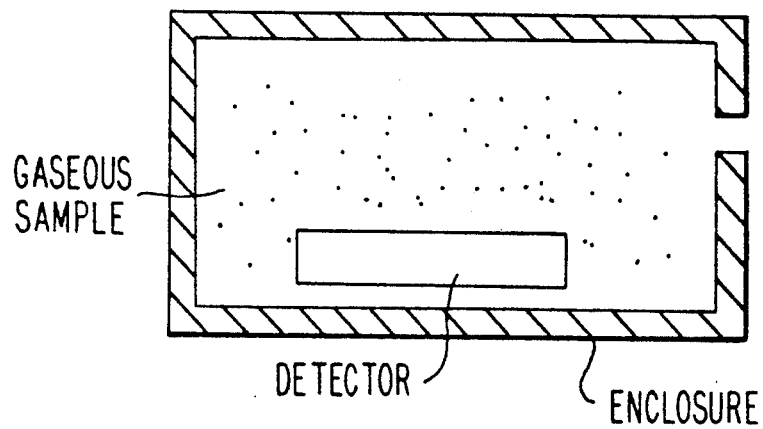
FIG. 1 is a longitudal section view of the device which includes a detector component positioned inside a sealed cylindrical housing having connector sections on either end of the housing.

The invention will be more particularly described with reference to a preferred embodiment which provides a convenient, easily transportable and comparatively simple device for use in the present method for obtaining a rapid and substantially fool-proof indication of the proper or improper placement of an endotracheal catheter in the trachea of a patient. As set forth below, the invention may also find utility in the detection of apnea.

The present invention relates to detectors for carbon dioxide in general and especially respiratory gas detectors and methods and apparatus concerning the same. It should be understood that a wide variety of techniques for collecting a sample of gas for contact with the detector in accordance with the invention may be utilized without departing from the scope of the invention. By way of example only, one such embodiment may include a cylindrical housing having at one end a truncated cone-shaped coupling which terminates in a substantially cylindrical connector. The other end of the housing is similarly joined to a truncated cone-shaped coupling which terminates in a substantially cylindrical connector.

In this embodiment, the coupling is formed integrally with the connector and is made from plastic, for example, polyethylene or polypropylene. The coupling/connector unit may be separable from the housing and releasably secured thereto by a suitable threaded engagement.

Likewise, the coupling is preferably formed integrally with the connector and may be made from a similar plastic. If desired the coupling/connector unit may also be releasably secured to the housing by a suitable threaded engagement.

The housing is may be made from a clear, colorless, transparent plastic, for example, an acrylic polymer, such as that available under the trademark PLEXIGLAS. Other suitable materials for the housing include nylon, polycarbonate, polystyrene or styrene-acrylonitrile copolymer. When the housing and associated coupling/connector units are interconnected they effectively form an enclosure having an inlet defined by one connector, such as the connector, and an outlet defined by the other connector. It should be understood that the present invention is not to be limited by the nature or shape of the enclosure and its inlet and outlet. It is sufficient if the enclosure is merely capable of collecting a suitable sample of gas to be tested.

A carbon dioxide detector component is suitably mounted within the enclosure. The plastic used for the enclosure is preferably clear and transparent so as to provide an effective capability for viewing the detector component. Of course, the enclosure need not be completely transparent and, if not, may be provided with an appropriate viewing window. The invention is not to be limited in this regard.

In one embodiment, such as the embodiment set forth in the following examples, the detector component may consist of a suitable strip of Whatman filter paper impregnated with a chemical treatment or indicator composition such as that set forth in the Examples herein. The detector component may take any appropriate form. One suitable form is to wrap the treated filter paper around a cylindrical spool which may be made from plastic, such as polyethylene. The spool is mounted within the housing at each end on an inwardly projecting annular flange formed as part of a disc-like insert. Each of the inserts is mounted within the housing substantially adjacent an associated one of the truncated conical couplings and is preferably made from plastic, similar to that used for the cylindrical housing. The inserts are preferably substantially circular to conform to the shape of the housing and each is provided with a plurality of apertures which allow substantially unrestricted flow of gas through the enclosure. The apertures may be a series of circular holes annularly aligned, or may be a different arrangement of holes or openings of a different shape.

In the present embodiment, the inner periphery of each of the couplings is provided with a circumferential groove or recess. When the enclosure is assembled, each of the disc-like inserts is retained in position within one of the grooves against the respective end of the cylindrical housing. The inserts, together with the detector supporting spool, are secured in place within the enclosure when each coupling is screwed to the housing.

After assembly, the enclosure and detector component may be sealed within a gas-impermeable envelope of metallic foil or the like, until required for use. The detector component may be oriented in the enclosure, as desired, such that gas passing through the enclosure contacts either one or both sides of the detector.

In operation, one of the connectors is placed in fluid flow communication with, for example, an endotracheal tube. The patient is intubated with the tube so that internal gas passes into the housing and into contact with the carbon dioxide detector component. If the gas is respiratory, a change in color of the detector is observed within a diagnostically effective period of time, for example less than about 20 seconds and preferably from about two (2) to about ten (10) seconds. This indicates proper tracheal intubation. If no color change occurs in such a period of time esophageal intubation is likely and the position of the tube should be readjusted. The steps are repeated until the desired color change is observed. It will be understood that a carbon dioxide detector of the type described herein may be placed within a suitable mask and used for the detection of apnea or for sampling gas flowing through such a mask to the patient or other person wearing the mask without departing from the scope of the invention.

To achieve the desired rapid response for diagnostic purposes, of the order of two (2) to twenty (20) seconds, and at the same time avoid such sensitivity that the device reacts too quickly to ambient air which normally contains about 0.03% carbon dioxide and other trace acidic gases, a chemical treating composition is employed in a preferred embodiment wherein the indicator used to prepare an alkaline solution comprises a particular combination of materials as will be described in greater detail below.

It is believed that the hydroxyl ions or amine residues present in the chemical treating composition from which a preferred type of detector component is formed react chemically with carbon dioxide to produce a carbonate and/or bicarbonate or carbamate moiety, respectively, as represented by the following equations:

(i) $CO_2 + 2OH^- \rightleftharpoons CO_3^{--} + H_2O$ (ii) $CO_3^{--} + CO_2 + H_2O \rightleftharpoons 2HCO_3$ (iii) $CO_2 + 2R_2NH \rightleftharpoons R_2NCOO^- + R_2NH_2+$ This reaction tends to deplete the hydroxyl ion or amine at the interface between the detector and the gaseous sample and thereby lower the pH of the detector. Such depletion is continuously opposed by diffusion of base to the interfacial surfaces of the detector which tends to maintain the pH constant at such surfaces. In most instances a chemical equilibrium will be established with the passage of time. In the preferred embodiment, an observable color change will occur when the surface pH is sufficiently lowered. This will occur generally when the concentration of $OH^-$ or amine in the treatment solution is insufficient to replenish the hydroxyl ion or amine at the interface in the presence of the desired concentration of carbon dioxide at the interface for a selected diagnostically effective period of time. Generally, the final color hue will be present once chemical equilibrium or steady state is attained.

For optimum results, in terms of speed of transition and ease of detection of color change, it has been found that the concentration of $OH^-$ in the chemical treatment composition should be such that the treatment solution has a pH of $9.6 \pm 0.6$ when in equilibrium with room air prior to impregnation of the inert preferably bibulous carrier. When, under such circumstances, the pK of the chromogenic dye in the particular solvent system in use is in the range of 7.3 to 8.9 and the carrier has the characteristics of Whatman No. 1 filter paper, the detector will change color dramatically, e.g. from blue to yellow, within a diagnostically effective time of from about two (2) to about ten (10) seconds in the presence of at least about 2% carbon dioxide in the gas sample, as is shown in some of the following examples. Under these conditions the pK value of the dye is sufficiently lower than the pH of the treatment solution to ensure that a noticeable color change would not occur for at least fifteen minutes when the detector is exposed only to ambient air. Of course the present invention is not to be limited by a particular combination of treatment solution and carrier material which yield such optimum results. A less dramatic color change may be acceptable and the difference between the pK of the chromogenic dye and the pH of the treatment solution may be adjusted, for example within the range of from about 0.5 to 1.5, as may be desired to achieve an intended result.

Suitable compounds for the treatment solution which may, for example, be used subject to the selection of an appropriately corresponding indicator are calcium hydroxide, sodium carbonate, lithium hydroxide, sodium hydroxide, potassium hydroxide, magnesium hydroxide, potassium carbonate, sodium barbital, tribasic sodium phosphate, dibasic sodium phosphate, potassium acetate, monoethanolamine, diethanolamine, triethanolamine glycine, tromethamine, and piperidine. Barium hydroxide has a similar chemical profile to calcium hydroxide and may also be used provided appropriate care is taken to shield a patient from any residual toxicity.

Examples of suitable pH-sensitive indicators are metacresol purple, thymol blue, cresol red, phenol red, xylenol blue, a 3:1 mixture of cresol red and thymol blue, bromthymol blue, neutral red and phenolphthalein. A particularly preferred combination of carrier, base and indicator is, respectively, Whatman No. 1 filter paper, calcium hydroxide and metacresol purple.

It has been found that different carriers, for example Whatman No. 3, may also be used satisfactorily provided appropriate adjustments are made to other parameters so as to maintain the desired performance characteristics. By way of example, Whatman No. 3 is subject to chromatography effects when pressed dry. Therefore, the concentration of $OH^-$ should be higher in the treatment solution resulting in a higher pH. This, in turn, suggests the selection of a chromogenic dye having a correspondingly higher pK, for example thymol blue. A 3:1 mixture of thymol blue and cresol red has a pK very similar to metacresol purple. Where the resulting orange tinted yellow color achieved upon transition is tolerable this mixture may also be found useful. If a less visually dramatic color transition than the purple to yellow transition of metacresol purple is desired then cresol red may be used.

A hygroscopic liquid has been found useful in the treatment solution to ensure that the detector contains a chemical treatment composition which is generally non-volatile and capable of entrapping sufficient water during use to enable the exposed surface of the detector to act as a reaction zone with the surrounding gas. Examples of suitable hygroscopic liquids are glycerol, propylene glycol, dipropylene glycol, monoethylene glycol, diethylene glycol and mixtures thereof. Triethylene glycol and higher polyethylene glycols and various aliphatic alcohols, because they are non-toxic and have antiseptic properties which inhibit bacterial and fungal growth, also may be used. Glycerol and propylene glycol or mixtures thereof are particularly preferred.

The following Examples illustrate the preparation of particular examples of treatment and substrate carried solutions.

EXAMPLE 1

A 0.003M aqueous solution of calcium hydroxide was prepared by dissolving calcium oxide in 5 ml. of freshly boiled, distilled water. The pH of the resulting solution was 11.6 to 11.7. Metacresol purple sodium salt was added to the solution so that the concentration of the indicator was 0.12%. An equal volume of propylene glycol was added and the solution stirred to obtain a homogeneous mixture. A 10% additional volume of glycerol was added to the mixture. The glycerol improved penetrability and diffusion into the filter paper. The resulting treatment solution having a pH of about 9.6 was applied to a double layer of Whatman No. 1 filter paper and the surface of the paper was then dried by passing a stream of heated air over it for several seconds.

The impregnated paper may be cut into strips and immediately used in a device according to the invention, as described hereinafter, or may be stored for future use. Protection from exposure to ambient atmosphere may be obtained by storing the paper in a sealed container under an atmosphere of nitrogen or over soda-lime granules.

The impregnated strip made in accordance with this Example stays purple for more than two hours in a atmosphere containing 0.03% carbon dioxide and trace levels of other acidic gases. Upon exposure to an atmosphere containing 5% carbon dioxide, the strip turns bright yellow within three to five seconds. In 2% carbon dioxide the yellow color is achieved in 7 to 10 seconds and is of slightly darker hue.

EXAMPLE 2

A 0.0065M aqueous solution of sodium carbonate was prepared by dissolving sodium carbonate in 5 ml. of carbon dioxide-free, distilled water. The pH of the resulting solution was approximately 11.0 0.05% w/v of thymol blue was added to the solution. An equal volume of glycerol was added and the solution was stirred to provide a homogeneous mixture of treatment solution having a pH of about 9.4. The resultant treatment solution was absorbed on a strip of Whatman No. 1 filter paper and the impregnated paper was dried by blotting.

When exposed to varying concentrations of carbon dioxide, the impregnated strip responded as follows:

| $CO_2$ Concentration | Contact Time | Color of Strip |
| --- | --- | --- |
| 0 | o0 | blue |
| 0.03% (ambient air) | 10 minutes | blue-green |
| 0.03% | 15 minutes | green |
| 2.0% | 5 seconds | yellow |
| 5.0% | 1 second | yellow |

In this example the difference between the pK of the thymol blue and the pH of the treatment solution after glycerol was added was about 0.5. Under these conditions some color change occurs in ambient air within about 15 minutes but a definite change from blue to yellow occurred within one (1) to five (5) seconds when the carbon dioxide concentration was in the range from 5.0% to 2.0% respectively. Accordingly, this system is more sensitive than that of Example 1 but yields acceptable results.

EXAMPLE 3

Example 2 was repeated except that propylene glycol was substituted for the glycerol.

The performance characteristics of the impregnated strip were substantially similar to those of the strip of Example 2.

EXAMPLE 4

A solution of sodium carbonate, water and glycerol was made up as in Example 2 but instead of thymol blue, the indicator was metacresol purple (sodium salt). Metacresol purple has a lower pK than thymol blue. The substitution of metacresol purple altered the sensitivity in ambient air but produced a very slight greenish tint to the yellow color after 5 seconds exposure to 5% carbon dioxide.

An interesting property of this system is its extremely rapid return to the original purple color when returned to ambient air. Accordingly, this pH 9.4, sodium carbonate, glycerol, metacresol purple indicator system is a useful alternative to the preferred calcium hydroxide system illustrated in Example 1.

The response characteristics of a strip of Whatman No. 1 filter paper impregnated with the solution of this Example are as follows:

| $CO_2$ Concentration | Contact Time | Color of Strip |
| --- | --- | --- |
| 0 | ∞ | bright purple |
| 0.3% | 2 hours | bright purple (slightly lighter hue) |
| 2.0% | 10 seconds | greenish yellow |
| 5.0% | 5 seconds | greenish yellow (lighter hue) |

The addition of carbonic anhydrase (10 activity units per ml. of solution) to the indicator solution causes the transition at about 2% and about 5% and back to room air to occur nearly instantaneously. The enzyme is catalyzing the rate at which equilibrium pH is attained.

EXAMPLE 5

This Example is included to illustrate the significance of balancing the various parameters.

By using a similar system to that illustrated in Example 2 but increasing the concentration of sodium carbonate to produce a 0.1M aqueous solution having a pH of 11.6 before the introduction of glycerol, the system after the introduction of glycerol behaved as follows:

| $CO_2$ Concentration | Contact Time | Color of Strip |
| --- | --- | --- |
| 0.03% | 3 hours | blue |
| 0.3% | 10 minutes | blue |
| 5.0% | 20 seconds | blue (slightly lighter hue) |
| 100% | 1 second | yellow |

Since the strip did not change color in less than 20 seconds in the presence of 5.0% carbon dioxide, it lacks the ability to respond within the preferred diagnostically effective time period.

In contrast, a thymol blue system using a 0.00016M aqueous solution of sodium carbonate having a pH of approximately 10.0 before the introduction of glycerol was found to evidence a color change in the presence of room air or 0.3% carbon dioxide in a period of time which was too short to constitute a valid test for respiratory gas under the circumstances of medical emergency which would dictate the need for the method and apparatus of the present invention.

EXAMPLE 6

A 0.1M aqueous solution of sodium hydroxide was prepared by dissolving sodium hydroxide in 5 ml. of carbon dioxide-free distilled water. 0.05% w/v thymol blue was added followed by an equal volume of propylene glycol. The resultant solution was absorbed on Whatman No. 1 filter paper.

The impregnated paper strip was exposed to varying concentrations of carbon dioxide and performed as follows:

| $CO_2$ Concentration | Contact Time | Color of Strip |
| --- | --- | --- |
| 0.03% | 45 minutes | blue |
| 0.3% | 50 seconds | blue |
| 5.0% | 1 second | green |

Lithium hydroxide was substituted for sodium hydroxide with similar results.

EXAMPLE 7

An aqueous solution containing 0.67% monoethanolamine was prepared by dissolving the monoethanolamine in 5 ml. of carbon dioxide-free, distilled water. 0.005% w/v metacresol purple was added to the solution followed by an equal volume of propylene glycol.

The resultant mixture was absorbed on filter paper in a similar manner to that illustrated in previous Examples. Exposure to various concentrations of carbon dioxide gave the following results:

| $CO_2$ Concentration | Contact Time | Color of Strip |
| --- | --- | --- |
| 0% | ∞ | deep purple |
| 0.03% | 0.5 seconds | light purple |
| 0.03% | 1 hour | light purple |
| 0.3% | 3 minutes | light purple |
| 2.0% | 8 seconds | greenish yellow |
| 5.0% | 1 second | yellow |

EXAMPLE 8

Example 7 was repeated using 2.5% solution of monoethanolamine and thymol blue as indicator. The following results were obtained.

| $CO_2$ Concentration | Contact Time | Color of Strip |
| --- | --- | --- |
| 0% | ∞ | blue |
| 0.03% | 1 second | blue-green |
| 0.03% | 3 hours | blue-green |
| 2.0% | 8 seconds | green |
| 5.0% | 2 seconds | yellow-green |

Within one second of exposure to ambient air the surface pH drops from 12.4 to approximately 9.2 (blue-green color) but does not change thereafter to any measurable degree from this steady state value. However, exposure to 5% carbon dioxide rapidly causes a chromatic transition (yellow color) to occur, i.e. within one to two seconds.

In all of the above systems, the concentration of pH indicator used can be increased as desired to obtain a greater depth of color in the impregnated carrier. However, any such increase in concentration should not be such as to blunt the degree of chromatic transition due to bufferring of the fall of pH in the presence of physiologically significant levels of carbon dioxide.

It will be understood by persons skilled in the art that various modifications may be made in the foregoing components, described as exemplary of the invention, without departing from the scope of the invention which is to be measured only by the following claims.

What is claimed is:

1. Apparatus for determining whether a gaseous sample contains a predetermined concentration of carbon dioxide, comprising:
   means for introducing the gaseous sample into an enclosure;
   dry reagent detector means within the enclosure for producing a response to the presence of said predetermined concentration of carbon dioxide in the sample, said detector means comprising a carrier having a aqueous indicating composition applied thereto, said indicating composition providing an indication of the presence of said predetermined concentration of carbon dioxide in the sample within a diagnostically effective period of time when the carbon dioxide concentration in the sample is at least about 2% and providing said indication after about ten minutes when the carbon dioxide concentration in the sample is about 0.03%.

2. The apparatus of claim 1, in which said carrier comprises an inert bibulous material.

3. The apparatus of claim 1, in which said carrier comprises an inert fibrous material.

4. The apparatus of claim 1, in which said carrier comprises an inert porous material.

5. The apparatus of claim 1, in which said diagnostically effective period of time is up to about twenty seconds.

6. The apparatus of claim 5, in which said diagnostically effective period of time is from about two to about ten seconds.

7. The apparatus of claim 1, in which said indication is visually observable.

8. The apparatus of claim 1, in which said detector means is substantially non-fluid.

9. The apparatus of claim 1, in which said indicating composition comprises predetermined amounts of a base and a hygroscopic material.

10. The apparatus of claim 9, in which the pH of said base is in the range of from about 9.0 to about 10.2.

11. The apparatus of claim 1, in which said indicating composition comprises carbonic anhydrase.

12. The apparatus of claim 1, in which said detector means comprises a pH sensitive substance.

13. The apparatus of claim 1, in which said indicating composition consists essentially of a chromogenic material and a hygroscopic, water-miscible liquid.

14. The apparatus of claim 13, in which said indicating composition comprises an aqueous alkaline solution.

15. The apparatus of claim 14, in which said chromogenic material comprises a chromogenic pH indicator.

16. The apparatus of claim 15, in which a predetermined relationship exists between the pH of said indicating composition and the pK of said chromogenic pH indicator.

17. The apparatus of claim 16, in which said chromogenic pH indicator has a pK in said solution which is lower by about 0.5-2.8 pH units than the pH of said aqueous alkaline solution.

18. The apparatus of claim 17, in which said chromogenic pH indicator has a pK in solution which is lower by about 1.0-1.5 pH units than the pH of said aqueous alkaline solution.

19. The apparatus of claim 16, in which said aqueous alkaline solution is a solution of calcium hydroxide and said chromogenic pH indicator is selected from the group comprising metacresol purple and chromogenic pH indicators having pK values substantially the same as metacresol purple.

20. The apparatus of claim 1, in which said carrier comprises cellulose.

21. The apparatus of claim 1, comprising means for protecting said detector means from ambient air until no more than about fifteen minutes prior to exposure to said sample.

22. An element for use in detecting the presence of respiratory concentrations of carbon dioxide in a gaseous sample, comprising:
a substrate; and
a dried non-volatile chemical composition carried by said substrate, said composition providing an indication within a predetermined period of time of the presence of a respiratory concentration of carbon dioxide in the sample and providing said indication after about ten minutes when the concentration of carbon dioxide in the sample is substantially less than said respiratory concentration.

23. A device for detecting the presence of a predetermined concentration of carbon dioxide in a gaseous sample comprising a non-liquid detector element having a non-volatile chemical composition the pH of which changes in the presence of said predetermined concentration and means responsive to said change in pH for providing an indication within a predetermined period of time of the presence of said predetermined concentration of carbon dioxide in the sample and providing said indication after about ten minutes when the concentration of carbon dioxide in the sample is substantially less than said respiratory concentration.

24. Apparatus for determining whether a gaseous sample contains a predetermined concentration of carbon dioxide, comprising:
means for introducing the gaseous sample into an enclosure;
detector means within the enclosure for responding to the presence of the predetermined concentration of carbon dioxide, said detector means comprising a carrier to which a non-volatile indicating composition has been applied, said indicating composition providing a first response within a diagnostically effective period of time when the carbon dioxide concentration in the sample is at least about 2% but not providing said first response for more than about ten minutes when the carbon dioxide concentration in the sample is about 0.03%, and providing a second response within said diagnostically effective period of time when the sample is replaced with ambient air.

25. The apparatus of claim 24, in which said first response consists of a first observable color change and said second response consists of a second observable color change.

* * * * *